(12) United States Patent
Bailey et al.

(10) Patent No.: US 7,678,144 B2
(45) Date of Patent: Mar. 16, 2010

(54) PROSTHETIC VALVE WITH SLANTED LEAFLET DESIGN

(75) Inventors: Frances Kristen Bailey, Bloomington, IN (US); Brian C. Case, Lake Villa, IL (US); Ram H. Paul, Jr., Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 39 days.

(21) Appl. No.: 12/019,987

(22) Filed: Jan. 25, 2008

(65) Prior Publication Data

US 2008/0183279 A1    Jul. 31, 2008

Related U.S. Application Data

(60) Provisional application No. 60/897,972, filed on Jan. 29, 2007.

(51) Int. Cl.
*A61F 2/24* (2006.01)
(52) U.S. Cl. ............... 623/2.16; 623/2.17; 623/1.24
(58) Field of Classification Search ........... 623/1.24, 623/1.26, 2.12–2.33, 23.68
See application file for complete search history.

(56) References Cited

U.S. PATENT DOCUMENTS

| 4,643,732 | A | 2/1987 | Pietsch et al. | ............ 623/2.2 |
| 5,769,780 | A | 6/1998 | Hata et al. | ............ 600/36 |
| 6,221,091 | B1 | 4/2001 | Khosravi | ............ 606/200 |
| 6,358,277 | B1* | 3/2002 | Duran | ............ 623/2.12 |
| 6,602,286 | B1 | 8/2003 | Strecker | ............ 623/1.24 |
| 6,752,828 | B2 | 6/2004 | Thornton | ............ 623/1.24 |
| 2002/0065554 | A1 | 5/2002 | Streeter | ............ 623/2.36 |
| 2003/0033009 | A1 | 2/2003 | Gabbay | ............ 623/2.36 |
| 2003/0040792 | A1 | 2/2003 | Gabbay | ............ 623/2.11 |
| 2003/0055496 | A1 | 3/2003 | Cai et al. | ............ 623/2.19 |
| 2003/0130726 | A1 | 7/2003 | Thorpe et al. | ............ 623/1.24 |
| 2003/0208261 | A1 | 11/2003 | Thorpe et al. | |
| 2004/0117010 | A1* | 6/2004 | Houston et al. | ............ 623/2.33 |
| 2004/0225352 | A1 | 11/2004 | Case et al. | ............ 623/1.24 |
| 2005/0010287 | A1 | 1/2005 | Macoviak et al. | ............ 623/2.36 |
| 2005/0143807 | A1 | 6/2005 | Pavcnik et al. | ............ 623/1.24 |
| 2005/0187614 | A1 | 8/2005 | Agnew | ............ 623/1.24 |
| 2006/0058889 | A1 | 3/2006 | Case et al. | ............ 623/23.68 |

FOREIGN PATENT DOCUMENTS

EP    0 520 126 A1    11/1991

OTHER PUBLICATIONS

International Search Report for corresponding international application No. PCT/US2008/052151, dated Jul. 2, 2008.

(Continued)

*Primary Examiner*—David Isabella
*Assistant Examiner*—Rebecca Straszheim
(74) *Attorney, Agent, or Firm*—Buchanan Intellectual Property Office LLC (57) ABSTRACT

The invention relates to a prosthetic valve for regulating fluid flow through a body lumen. The valve includes a frame and a valve member comprising at least one semi-rigid leaflet and at least one flexible leaflet. The at least one semi-rigid leaflet comprises a first portion and a second portion, the first portion attached to the frame and the second portion free of the frame. The at least one semi-rigid leaflet is slanted in a retrograde direction from the second portion to the first portion. The at least one flexible leaflet comprises a first portion and a second portion, the first portion attached to the frame and the second portion free of the frame. The at least one flexible leaflet is slanted in a retrograde direction from the first portion to the second portion when at rest.

18 Claims, 7 Drawing Sheets

OTHER PUBLICATIONS

Written Opinion of the International Searching Authority for corresponding international application No. PCT/US2008/052151, dated Jul. 2, 2008.

PCT Notification Concerning Transmittal of International Preliminary Report on Patentability for PCT/US2008/052151, Aug. 13, 2009.

* cited by examiner

PROSTHETIC VALVE WITH SLANTED LEAFLET DESIGN

RELATED APPLICATIONS

This application claims the benefit of provisional U.S. patent application Ser. No. 60/897,972, filed Jan. 29, 2007, which is incorporated herein by reference in its entirety.

TECHNICAL FIELD

The present invention relates to medical devices for implantation in a body vessel. More particularly, the present invention relates to intraluminal valve prostheses.

BACKGROUND

The venous system includes a multitude of one-way bicuspid valves that permit substantially unidirectional blood flow toward the heart. These valves are particularly important in the lower extremities to prevent the pooling of blood. When the leaflets of the bicuspid valves fail to close properly, the valve is considered "incompetent" as it permits leakage of retrograde flow resulting in the abatement of flow towards the heart.

This potentially serious condition is known as "chronic venous insufficiency." Symptoms can progress from unsightly "spider" or varicose veins to skin discoloration and painful skin ulcerations. The etiology of venous insufficiency is multifactorial, including a past history of thrombotic events, chronic venous stasis, and venous hypertension. Current treatments for venous insufficiency include elevation of the feet and compression stockings. While these can relieve symptoms, the underlying disease remains untreated. Surgical techniques are also employed in which native valves can be bypassed or replaced with autologous sections of veins having functioning valves.

Recently, various implantable medical devices and minimally invasive techniques for implantation of these devices have been developed to treat and repair undesirable conditions within body vessels. For example, implantable medical devices can function as a replacement venous valve, or restore native venous valve function by bringing incompetent valve leaflets into closer proximity. These devices are advantageously inserted intravascularly, for example from an implantation catheter.

However, post-implantation thrombosis and platelet deposition on surfaces of endovascular prosthetic valves may occlude the conduit defined by the endovascular prosthesis or compromise the functionality of an implanted valve by limiting the motion or responsiveness of moveable portions of the device such as valve leaflets. For example, stagnation of blood around implanted prosthetic valves may cause stiffening and thickening of valve leaflets, reducing the leaflets' functionality and possibly eventually occluding the body lumen.

SUMMARY

The present invention relates to an implantable medical device for regulating fluid flow through a body vessel. More specifically, preferred aspects relate to a prosthetic valve comprising a valve member having at least one semi-rigid leaflet and at least one flexible leaflet.

In one aspect, a prosthetic valve for implantation within a body lumen comprising a frame and at least one valve member comprising at least one semi-rigid leaflet and at least one flexible leaflet is provided. The at least one semi-rigid leaflet comprises a first portion and a second portion, the first portion attached to the frame and the second portion free of the frame. The at least one semi-rigid leaflet is slanted in a retrograde direction from the second portion to the first portion. The at least one flexible leaflet comprises a first portion and a second portion, the first portion attached to the frame and the second portion free of the frame. The at least one flexible leaflet is slanted in a retrograde direction from the first portion to the second portion when at rest. The at least one flexible leaflet is moveable between a first position that permits fluid flow in a first direction and a second position in which the at least one flexible leaflet second portion overlaps the at least one semi-rigid leaflet second portion thus substantially preventing fluid flow in a second, retrograde direction.

DETAILED DESCRIPTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

The terms "frame" as used herein refers to a structure that can be implanted, or adapted for implantation, within the lumen of a body vessel.

As used herein, the term "body vessel" means any tube-shaped body passage lumen that conducts fluid, including but not limited to blood vessels such as those of the human vasculature system, esophageal, intestinal, billiary, urethral and ureteral passages.

The terms "about" or "substantially" used with reference to a quantity includes variations in the recited quantity that are equivalent to the quantity recited, such as an amount that is insubstantially different from a recited quantity for an intended purpose or function.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Prosthetic Valves

Prosthetic valves may comprise a frame and at least one valve member. The prosthetic valve may be any medical device that is introduced temporarily or permanently into the body for the prophylaxis or therapy of a medical condition. For example, such prosthetic valves may include, but are not limited to, heart valve prostheses, venous valve prostheses, artificial organs such as artificial hearts, and ventricular assist devices. Typical subjects (also referred to herein as "patients") are vertebrate subjects (i.e., members of the subphylum cordata), including, mammals such as cattle, sheep, pigs, goats, horses, dogs, cats and humans.

Valve Members

Prosthetic valves may comprise at least one valve member attached to a frame. Prosthetic valves comprising at least one valve member may be used to regulate fluid flow in a vein, for example to treat venous valve incompetency. For example, one or more prosthetic valves comprising one or more valve members can be implanted in a vein with incompetent native venous valves so as to provide a valve to replace the incompetent native valves therein. The one or more valve members may permit fluid to flow through a body vessel in a first direction while substantially preventing fluid flow in the opposite direction.

Figure 1A:
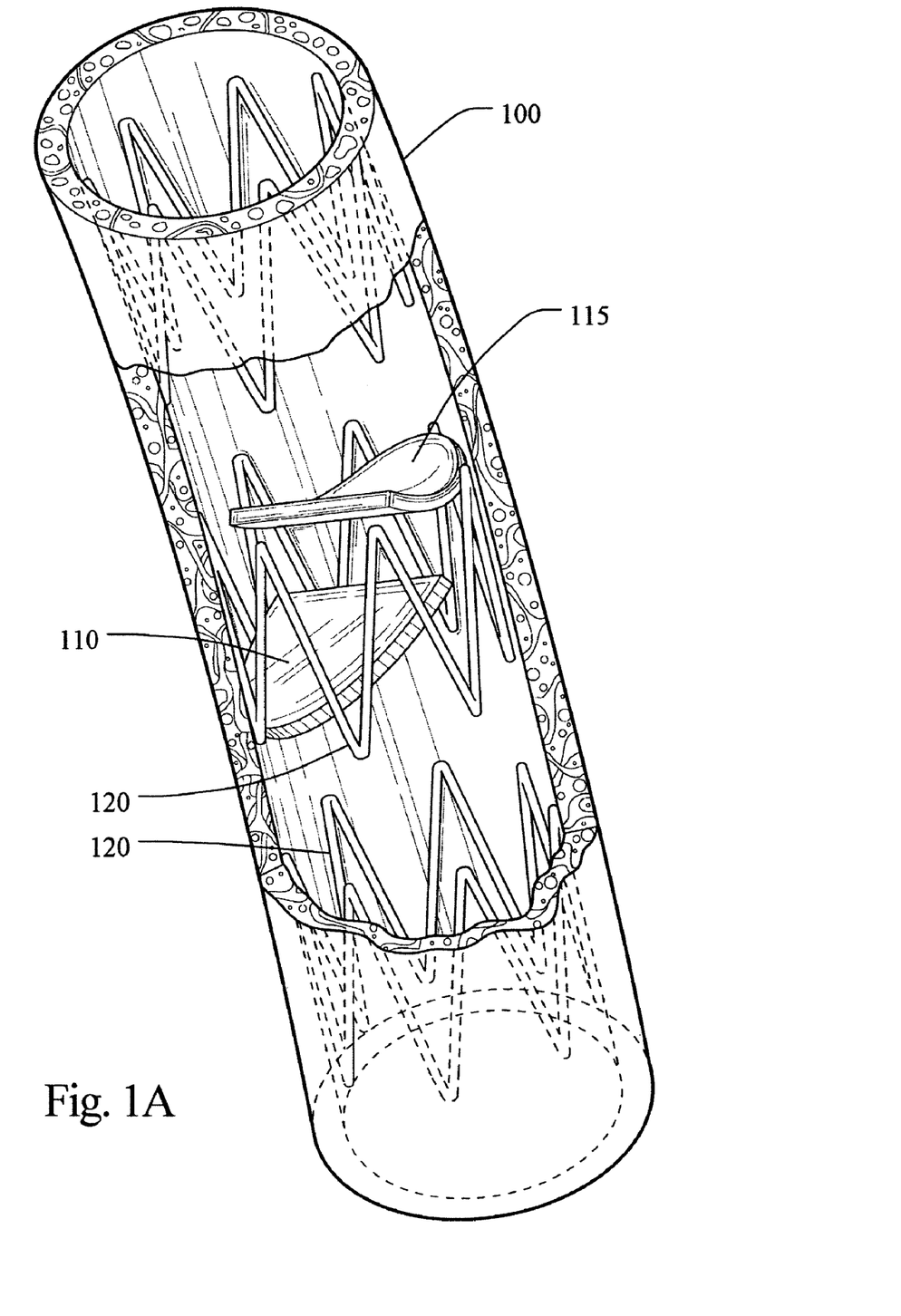
FIG. 1A is a perspective view of a body vessel containing a prosthetic valve, according to one aspect, in an open position.
Figure 1B:
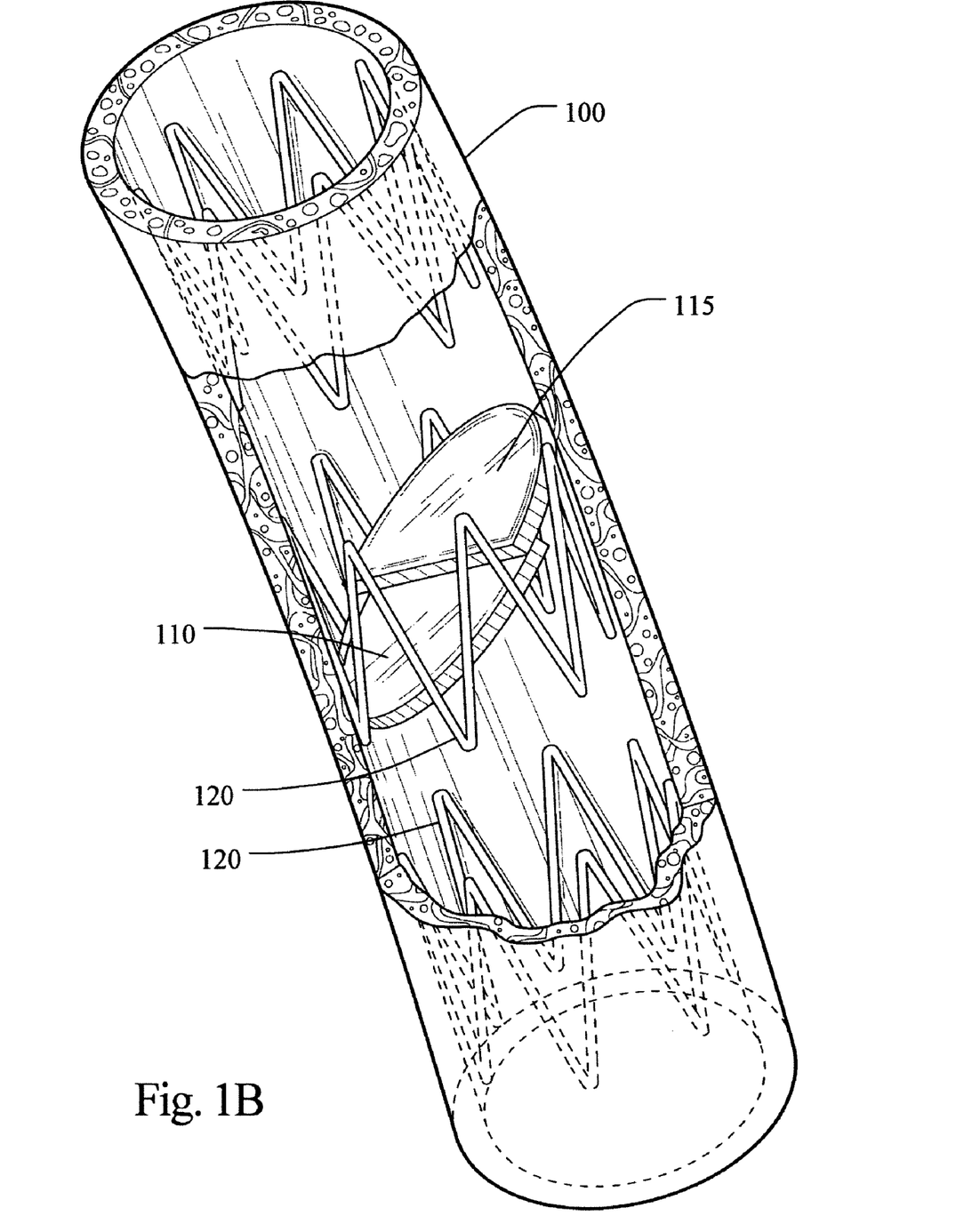
FIG. 1B is a perspective view of a body vessel containing the prosthetic valve of FIG. 1A in a second, closed position.

In one aspect, a valve member may comprise a plurality of semi-rigid leaflets and flexible leaflets. For example, FIGS. 1A and 1B depict one aspect of a prosthetic valve within a vascular vessel 100 comprising a valve member having a semi-rigid leaflet 110 and a flexible leaflet 115 operatively attached to a frame 120. FIG. 1A provides a perspective view of the prosthesis with the valve member in a generally open configuration. FIG. 1B depicts the valve member having a semi-rigid leaflet 110 and flexible leaflet 115 in a second, generally closed position.

As used herein, "semi-rigid" means partly or moderately rigid. A semi-rigid leaflet need only have rigidity sufficient to allow the semi-rigid leaflet to be substantially non-responsive to fluid flow through a body vessel. For example, a semi-rigid leaflet need only be sufficiently rigid such that, when subject to fluid pressures corresponding to the prosthesis' applicable use, the semi-rigid leaflet does not deflect to such a degree that a flexible leaflet free edge may no longer sufficiently contact the semi-rigid leaflet when the valve is in a closed configuration. A "free edge" refers to a portion of a leaflet that is not attached to the prosthetic valve, but forms a portion of a valve orifice. Flexible leaflets preferably comprise a free edge responsive to the direction of fluid flow in a body vessel.

Figure 2A:
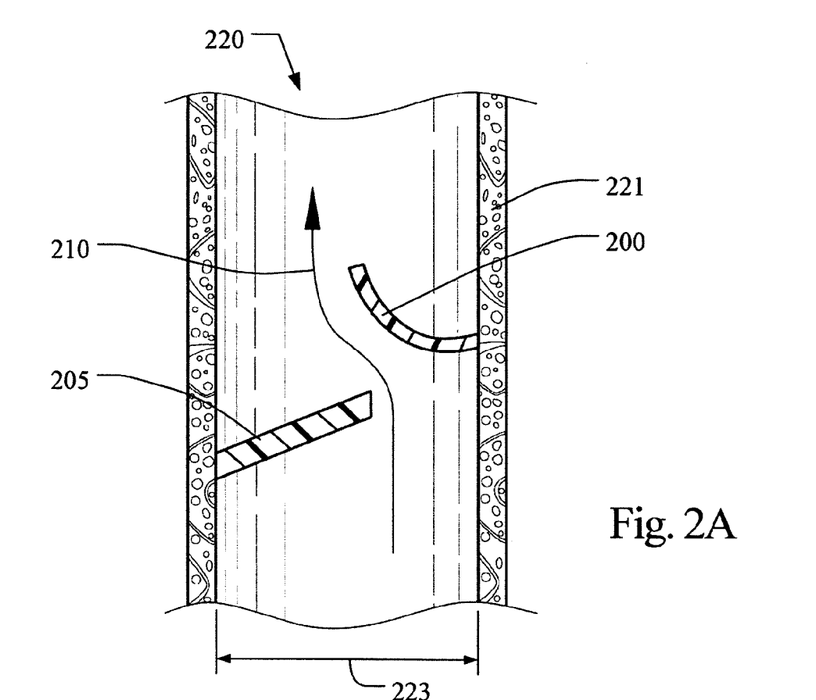
FIG. 2A is a partially sectioned view of a body vessel containing the prosthetic valve of FIG. 1A.

In operation, flexible leaflets are moveable between first and second positions when placed within a body vessel. In the first position, illustrated in FIG. 2A, the flexible leaflet 200 permits fluid flow in a first direction through the body vessel 220, represented by arrow 210. The pressure created by the fluid flow exerts a force on one face of the flexible leaflet 200, forcing it toward the vessel wall 221. In the second position, illustrated in FIG. 2B, the flexible leaflet 200 substantially prevents fluid flow in a second, opposite direction, represented by arrow 211, from flowing through the body vessel 220. The flexible leaflet 200 moves to the second position when a pressure change and/or reversal of flow direction exerts a force on the opposite face 201 of the flexible leaflet 200 and forces the leaflet away from the vessel wall 221 and across the lumen 222 of the vessel 220. Semi-rigid leaflet 205 is substantially non-responsive to fluid flow in the body vessel. The first position of the flexible leaflet 200 can be considered an open position, and the second position can be considered a closed position. By moving between these two positions, the flexible leaflet 200 provides a valving function, allowing the prosthesis to regulate fluid flow through the body vessel 220.

When the valve member closes in response to a pressure differential, the free edge of flexible leaflet 200 contacts, in the closed position, the semi-rigid leaflet 205 extending across the body lumen. The contacting portion of the leaflets is referred to as the coaptation region 300, 301, illustrated in FIGS. 3A and 3B, respectively. The coaptation region 300, 301 may vary depending on the desired use of the prosthesis. For example, the coaptation region may be between about 1% to about 100% of the vessel diameter 223. Preferably, coaptation region 300, 301 is about 25% or less of the vessel diameter 223 to minimize thrombus formation and leaflet inversion.

Figure 3A:
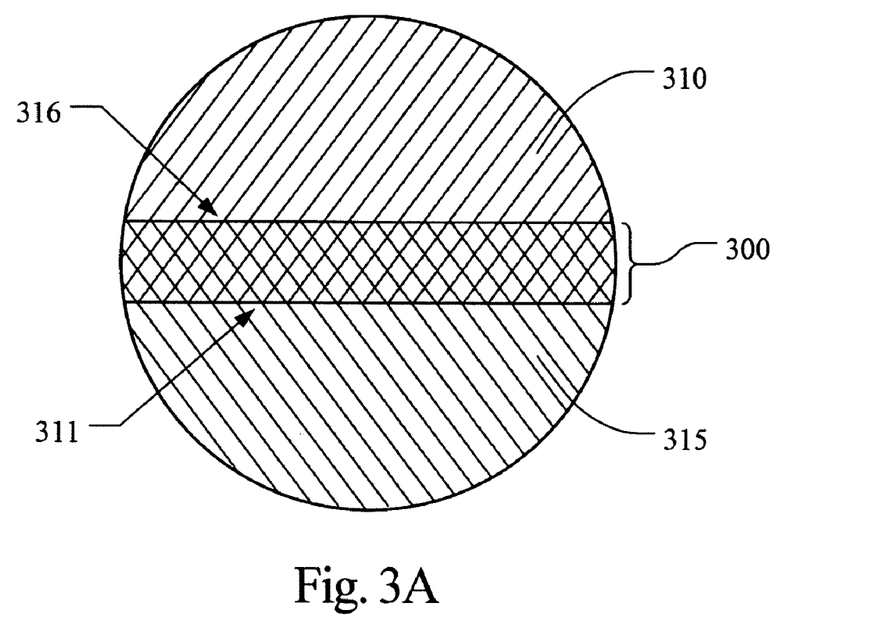
FIG. 3A is a schematic top view of a valve member according to one aspect.
Figure 3B:
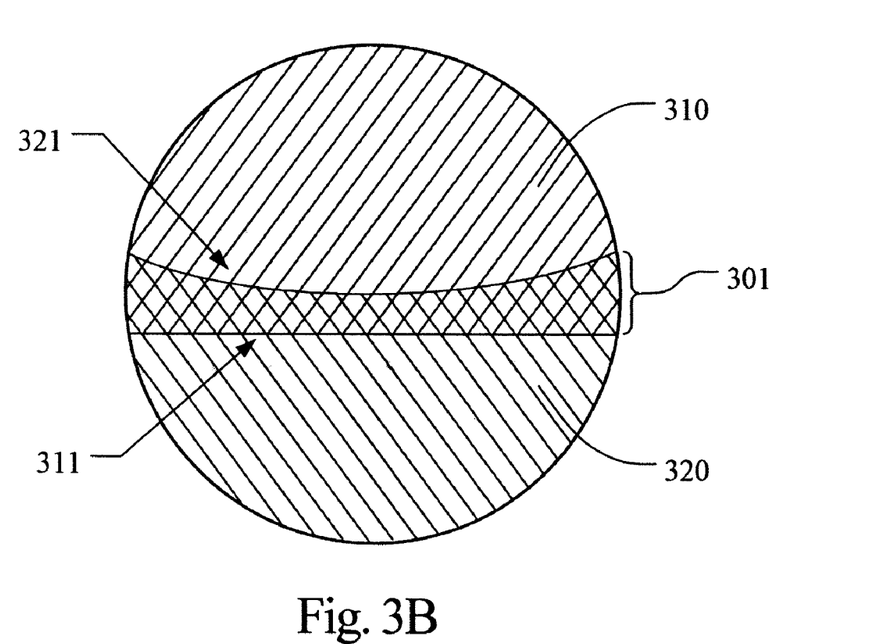
FIG. 3B is a schematic top view of a valve member according to another aspect.

Semi-rigid leaflets and flexible leaflets may have any suitable design. Variations may include, but are not limited to, leaflet free edge shape, leaflet length, leaflet curvature, leaflet angle, leaflet materials, and leaflet thickness. For example, leaflet free edges may have any shape, including, but not limited to, straight, zig-zag, curved, and sinusoidal. FIG. 3A shows one aspect, in which both the flexible leaflet 310 and semi-rigid leaflet 315 comprise straight free edges 311, 316, respectively. In another aspect, shown in FIG. 3B, a valve member may comprise a semi-rigid leaflet 320 with curved free edge 321. A curved free edge may improve prosthesis flow dynamics. In another aspect, the leaflet surface may comprise a curvature, such as a convex or concave curvature. In one example, the flexible leaflet comprises a surface having a curvature approximating the curvature of the body vessel.

Figure 2B:
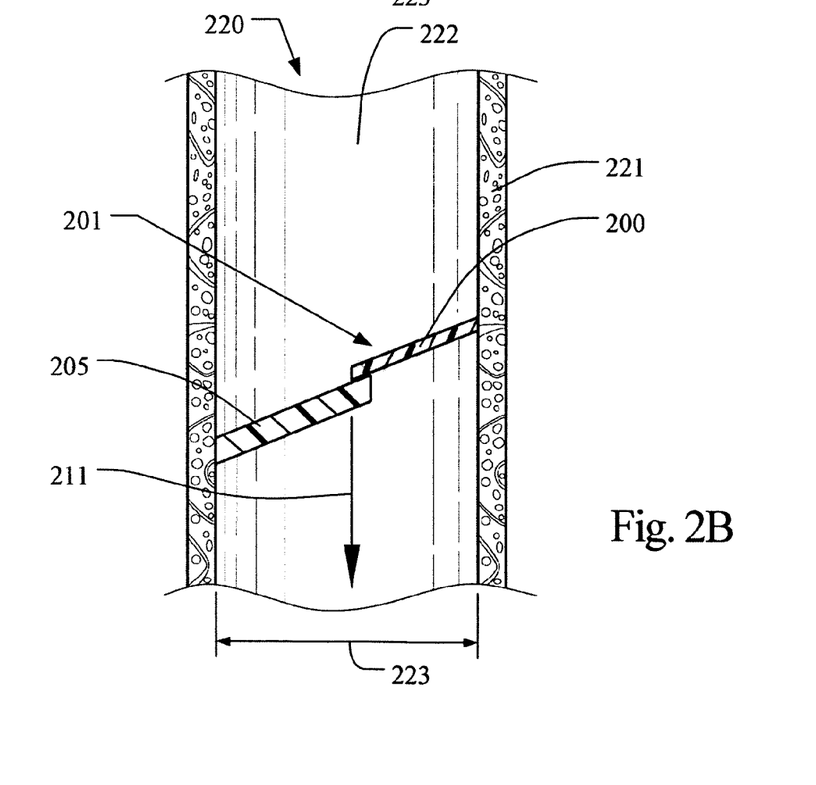
FIG. 2B is a partially sectioned view of a body vessel containing the prosthetic valve of FIG. 1B.

The length that valve member leaflets extend into the body vessel may also vary. Semi-rigid leaflet length and flexible leaflet length may be between about 1% to about 100% of the vessel diameter. In one aspect, the semi-rigid leaflet length is between about 25% to about 60% of the vessel diameter. In another aspect, the flexible leaflet length is between about 40% to about 75% of the vessel diameter. In a further aspect, both the flexible leaflet and semi-rigid leaflet have a length equal to about 51% of the vessel diameter (depicted in FIG.

Figure 5:
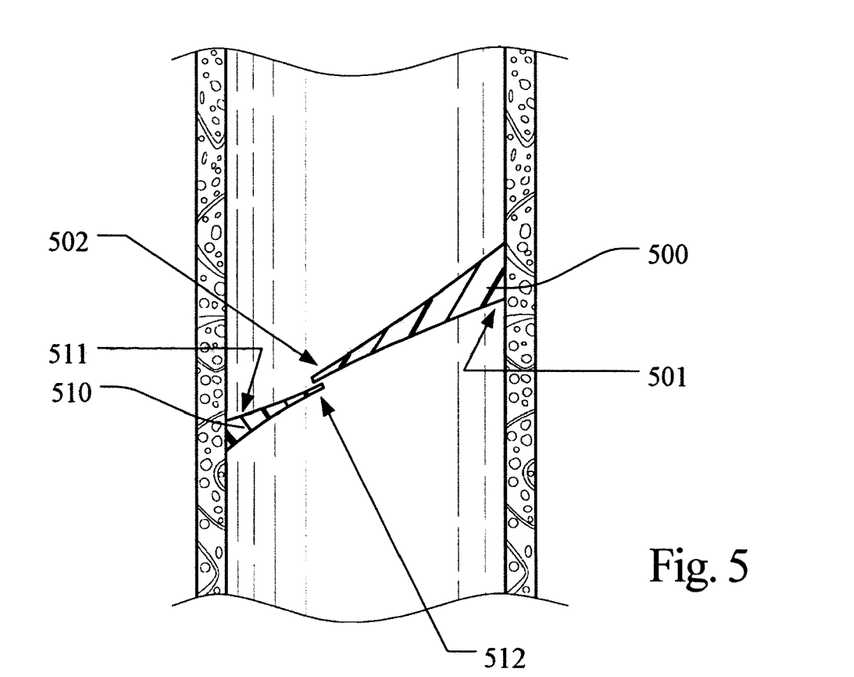
FIG. 5 is a partially sectioned view of a body vessel containing a prosthetic valve comprising tapered leaflets.

2B, for example). In another aspect, the semi-rigid leaflet extends into about 25% of the vessel diameter and the flexible leaflet extends into about 75% of the vessel diameter (for example, FIG. 5).

Flexible leaflets and semi-rigid leaflets are desirably slanted in the retrograde direction, and the angle at which the leaflets are oriented within the vessel may vary depending on the desired function and use of the prosthesis. The angle may be between about 0 degrees to about 90 degrees. Preferably, the leaflets are at an angle sufficient to minimize stagnation. For example, in one aspect, the flexible leaflets have an angle between about 0 degrees to about 60 degrees below horizontal. The semi-rigid leaflets preferably have an angle between about 0 to about 60 degrees above horizontal. In one aspect, the angles for semi-rigid leaflets and flexible leaflets comprising a valve member have the same degree measurement.

Figure 4:
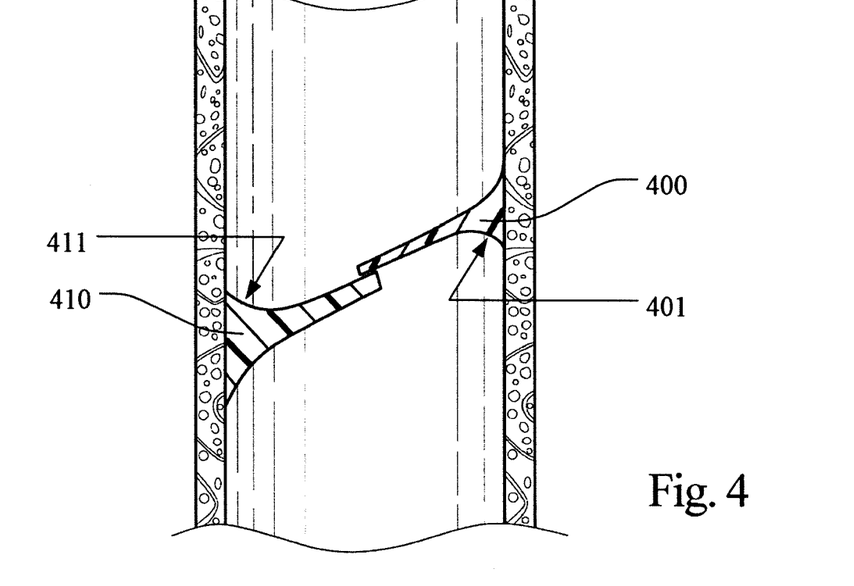
FIG. 4 is a partially sectioned view of a body vessel containing a prosthetic valve comprising leaflets having curved portions at the point of attachment to the prosthesis frame.

In another aspect, the leaflets are curved adjacent the frame and/or have varying thickness to further minimize stagnation. For example, in FIG. 4, the flexible leaflet 400 and semi-rigid leaflet 410 are curved 401, 411 adjacent attachment to the frame to minimize stagnation and provide for a curvature to the leaflets, providing improved flow dynamics. In a further aspect, shown in FIG. 5, the leaflets 500, 510 taper from the point of frame attachment 501, 511 to the leaflet free edge 502, 512.

In one aspect, valve members may substantially, but not entirely, prevent fluid flow in a second, opposite direction. As the flexible leaflet moves from the first position to the second position, a time period passes before the flexible leaflet returns to the second position, and some retrograde flow may pass through the prosthesis during this time. In one aspect, retrograde flow may pass through the leaflet coaptation region when the leaflets are in the closed position. In certain aspects, it may be desirable to permit a further, controlled amount of fluid flow to pass through the prosthesis in the second, opposite direction.

Figure 6A:
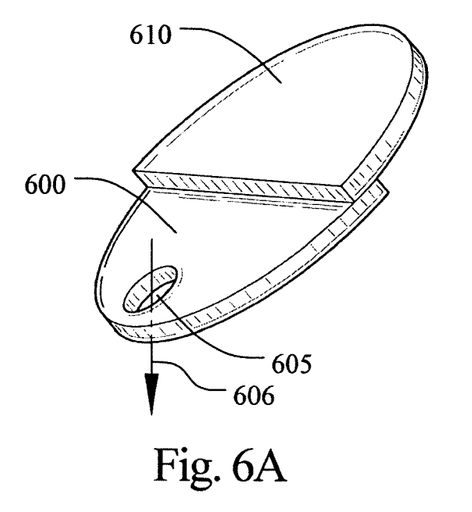
FIGS. 6A and 6B are perspective views of prosthetic valve comprising leaflets providing controlled retrograde flow.

For example, FIG. 6A illustrates a semi-rigid leaflet 600 comprising an opening 605. The opening 605 provides a passageway through which a controlled amount of retrograde flow 606 can pass when the flexible leaflet 610 is in the second position. The retrograde flow 606 passing through the opening 605 may facilitate closure of the valve member by allowing some of the retrograde flow 606 to continue moving past the valve member. Additionally, the opening 605 provides an escape through which fluid can move to prevent pooling during periods in which the flexible leaflet 610 is in the second, or closed, position.

The retrograde flow 606 that passes through the opening 605 when the flexible leaflet 610 is in the second position is controlled by the overall dimensions and configuration of the opening 605. A larger opening allows a greater amount of retrograde flow 606 to pass through the prosthetic valve, while a relatively smaller opening will allow a relatively lesser amount of retrograde flow 606 to pass. The dimensions and configuration of the opening 605 can be optimized based upon the vessel in which the prosthesis is placed. The size and configuration selected will depend on several factors, including the vessel size, typical flow volumes and rates, and others. The opening 605 is advantageously sized to allow a desired amount of retrograde flow to pass through the opening 605 during periods of retrograde flow 606. The opening 605 should be small enough, however, to still allow the leaflets 600, 610 to substantially prevent retrograde flow 606 from passing through the device while in the second position. Thus, the opening 605 is advantageously sized so as to prevent the majority of retrograde flow 606 to pass through the opening 605.

The opening 605 can be advantageously sized to mimic the degree of retrograde flow, or the leakiness, that is present in a natural valve located at the point of treatment in the body vessel. Accordingly, the dimensions of the opening 605 can be determined and optimized based upon the vessel in which the prosthesis 605 is to be placed. For venous valve applications, the total open area of the opening 605 is advantageously less than about 50% of the cross-sectional area of the vessel at the intended point of deployment. More advantageously, the total open area of the opening 605 is less than about 25% of the total cross-sectional area of the vessel at the intended point of deployment. For example, for venous valve applications, a circular opening with a diameter of between about 0.5 mm and about 3.0 mm has been found to be suitable. In a specific venous valve example, a circular opening with a diameter of about 1 mm has been found to be suitable. In another specific venous valve example, a circular opening with a diameter of about 2 mm has been found to be suitable.

Figure 6B:
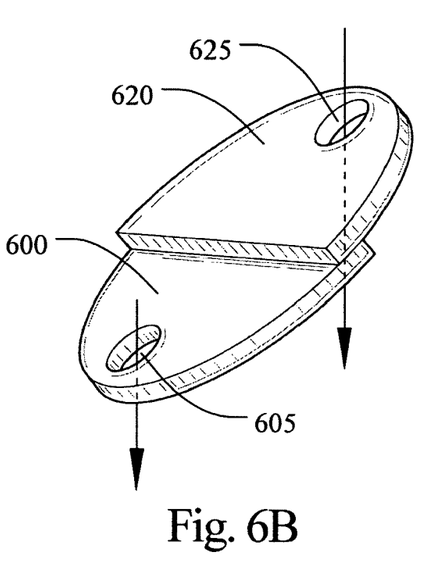

FIG. 6B illustrates a prosthetic valve according to another aspect. In this aspect, the valve includes multiple openings 605, 625 for allowing a controlled amount of retrograde flow to pass through the prosthesis when flexible leaflet 620 is in the second, closed position. Each of the openings 605, 625 is as described above, and the total cumulative open area of the openings 605, 625 is, at a maximum, less than the cross-sectional area of the vessel at the intended point of deployment.

Figure 7A:
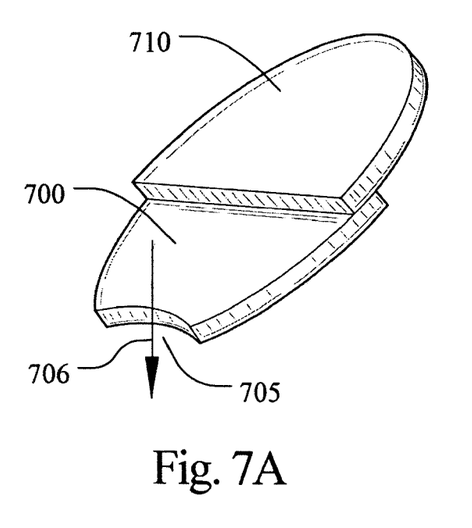
FIGS. 7A and 7B are perspective views of a prosthetic valve according to another aspect comprising leaflets permitting controlled retrograde flow.
Figure 7B:
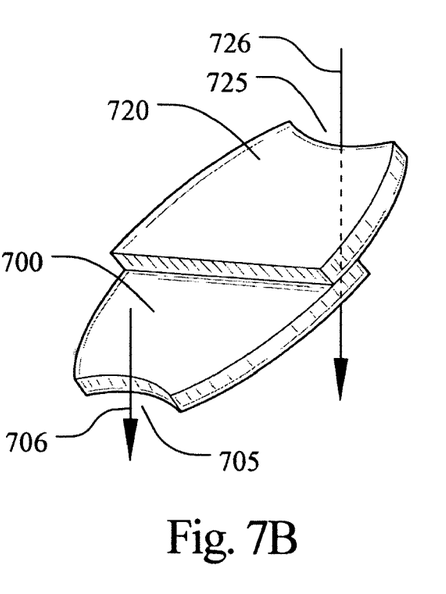

FIGS. 7A and 7B illustrate further aspects of a prosthetic valve. In these aspects, the openings 705, 725 reduce the overall surface area of the valve leaflet 700, 720 that contacts the vessel wall. It is believed that this reduction in surface area may reduce or eliminate the possibility that the valve leaflets 700, 720 would become adhered to or incorporated into the vessel wall. Also, the positioning of the openings 705, 725 relative to the frame may prevent stresses that might be placed on the valve leaflets 700, 720 during movement of the resilient support frame if the opening 705, 725 were not present. This may prevent damage to the valve leaflets 705, 725. Thus, in the examples illustrated in FIGS. 7A and 7B, each of the openings 705, 725 permits retrograde flow 706, 726 to pass through the prosthesis when the flexible leaflet 710, 720 is in the closed position, and protects the leaflets 700, 720 by spacing them away from the vessel wall. It is understood that, while one opening and two openings are illustrated in the above examples, the prosthesis may include more than two openings.

Although prosthetic valves in the illustrative figures are shown with valve members having two valve leaflets, the valve member may include any suitable number of leaflets. The valve member need only be able to provide the functionality described herein. The specific number chosen will depend on several factors, including the type and configuration of the frame. For example, the valve member may comprise 2, 3, 4, 5, 6, 7, 8, or more leaflets.

A wide variety of materials acceptable for use as semi-rigid leaflets and flexible leaflets are known in the art, and any suitable material can be utilized. Examples of suitable materials include natural materials and synthetic materials.

Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucosa (SIS), available from Cook Biotech, West Lafayette, Ind. When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets.

In addition to xenogenic biomaterials, autologous tissue can be harvested as well. Additionally, Elastin or Elastin Like Polypetides (ELPs) and the like offer potential as a material to fabricate the leaflets with exceptional biocompatibility. Another alternative is use of allographs such as harvested native valve tissue. Such tissue is commercially available in a cryopreserved state.

Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In one aspect, the valve member is made of one or more polymers that do not require treatment or modification to be biocompatible. For example, the valve member may include a biocompatible polyurethane. One example of a biocompatible polyurethane, THORALON (THORATEC, Pleasanton, Calif.), has been used in certain vascular applications and is characterized by thromboresistance, high tensile strength, low water absorption, low critical surface tension and good flex life.

A variety of other biocompatible polyurethanes/polycarbamates and urea linkages (hereinafter "—C(O)N or CON type polymers") may also be employed. Biocompatible CON type polymers modified with cationic, anionic and aliphatic side chains may also be used. See, for example, U.S. Pat. No. 5,017,664, which is incorporated herein by reference in its entirety.

Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PURSIL-10, -20, and -40 TSPU; PTMO and PDMS polyether-based aliphatic siloxane-polyurethanes, such as PURSIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

In certain examples, it may be desirable to reinforce semi-rigid leaflets and/or flexible leaflets, for example with threads, fibers, meshes, wires, etc., where additional strength or durability is needed. For example, polyurethane leaflets may be reinforced with fibers. The fibers may include any suitable material, but preferably include nanofibers from electrospinning. An electrospun layer of polyurethane may be applied to the prosthesis, and further processing may be applied to bring the leaflet construct up to desired specifications.

Figure 8A:
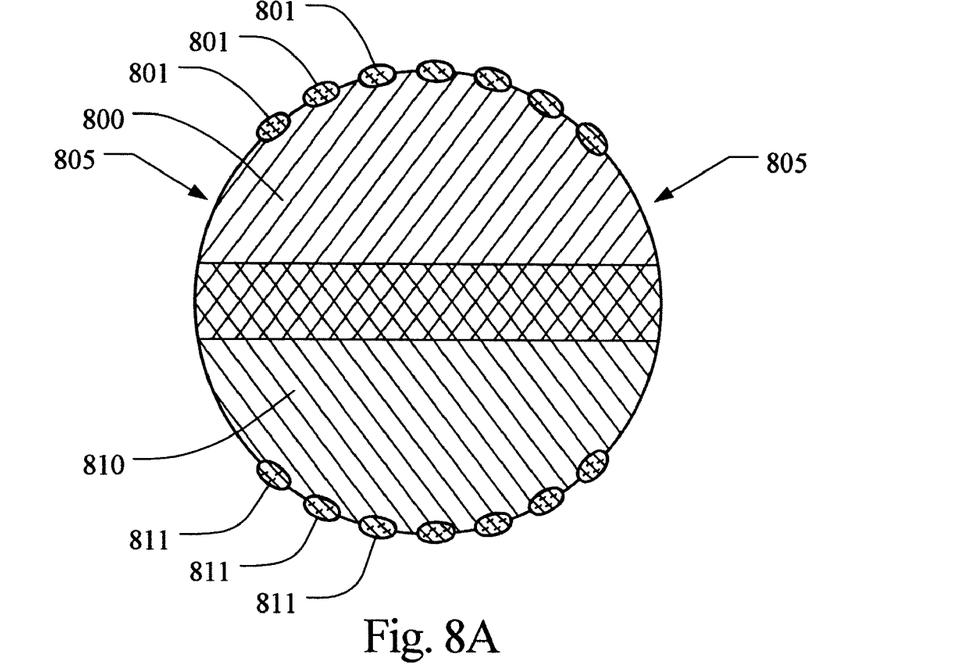
FIGS. 8A and 8B are schematic top views of a valve member depicting one aspect for attaching a valve member to the prosthesis frame.
Figure 8B:
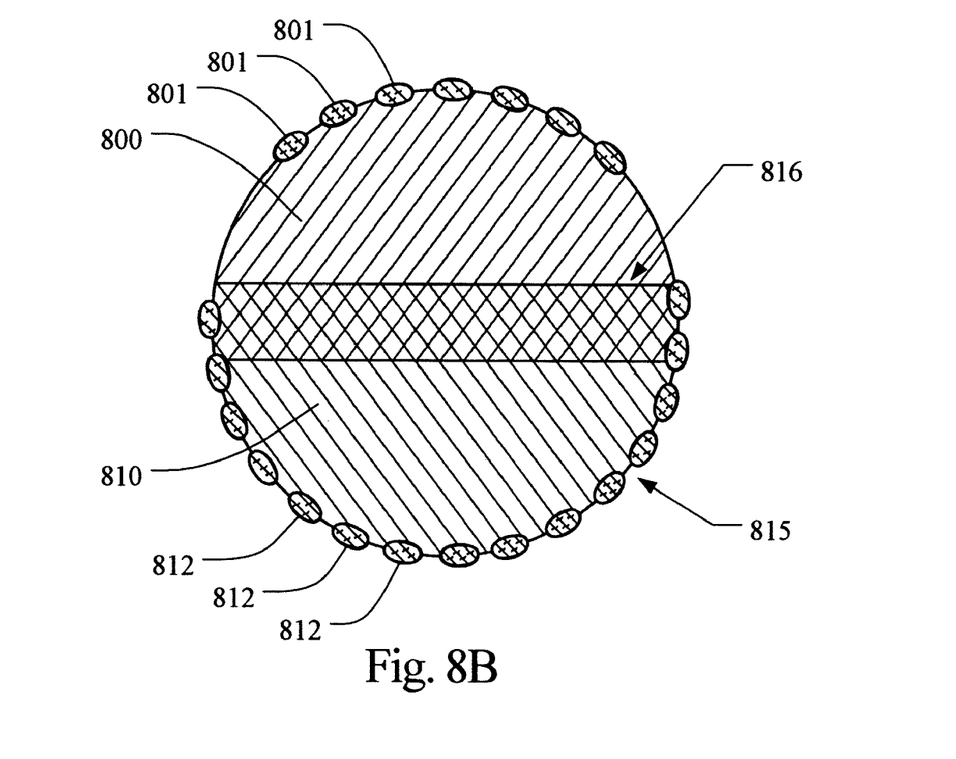

Semi-rigid leaflets and flexible leaflets may be attached to the prosthesis in any suitable manner. Suitable attachment mechanisms include, but are not limited to, dipping, adhesives, bonding, sutures, spraying, tissue welding, self-adhesion between regions of the material, chemical adhesion between the valve member and frame, spraying, cross-linking, and the like. For example, FIG. 8A shows flexible leaflet 800 and semi-rigid leaflet 810 attached to the prosthesis frame via sutures 801, 811. Preferably, flexible leaflet 800 may be attached such that a portion of the leaflet perimeter is free 805 from the frame, to move in response to fluid flow. FIG. 8B shows semi-rigid leaflet 810 attached via sutures 812 to the prosthesis substantially around its perimeter 815, excluding the semi-rigid leaflet free edge 816. Attaching a greater portion of the semi-rigid leaflet perimeter to the frame may provide the semi-rigid leaflet with greater rigidity.

In another preferred aspect, a biocompatible polyurethane may be applied as a solution to the frame. If necessary, gentle heating and/or agitation, such as stirring, may be employed to cause substantial dissolution. The attachment mechanism chosen for the semi-rigid leaflet will depend upon a number of factors, including but not limited to, leaflet materials, portion attached to the frame, and desired rigidity.

Frame

A wide variety of frames are known in the medical technology arts, and any suitable frame may be utilized. Suitable frames can have a variety of configurations, including braided strands, helically wound strands, ring members, consecutively attached ring members, and zig-zag members. Also, suitable frames can have a variety of sizes. The exact configuration and size chosen will depend on several factors, including the desired delivery technique, the nature of the vessel in which the device will be implanted, and the size of the vessel.

For example, suitable frames capable or supporting one or more valve members are disclosed in U.S. Pat. No. 6,464,720 to Boatman et al. for a RADIALLY EXPANDABLE STENT; U.S. Pat. No. 6,231,598 to Berry et al. for a RADIALLY EXPANDABLE STENT; U.S. Pat. No. 6,299,635 to Frantzen for a RADIALLY EXPANDABLE NON-AXIALLY CONTRACTING SURGICAL STENT; U.S. Pat. No. 4,580,568 to Gianturco for a PERCUTANEOUS ENDOVASCULAR STENT AND METHOD FOR INSERTION THEREOF; U.S. Publication No. 20010039450 to Pavcnik et al. for an IMPLANTABLE VASCULAR DEVICE; U.S. Pat. No. 5,800,508 to Goicoechea et al. for a BIFURCATED ENDOLUMINAL PROSTHESIS; U.S. Pat. No. 5,665,115 to Cragg for an INTRALUMINAL STENT; U.S. Pat. No. 5,507, 767 to Maeda et al. for a SPIRAL STENT; and U.S. Pat. No. 6,508,833 to Pavcnik et al. for a MULTIPLE-SIDED INTRALUMINAL MEDICAL DEVICE, each of which is hereby incorporated by reference in its entirety for the purpose of describing suitable frames for use in medical devices according to the invention.

A frame structure and configuration can be chosen to facilitate maintenance of the device in the vessel following implantation. For example, frame material that is too stiff can damage the vessel, not conform well to the vessel wall, and increase the profile of the device when loaded in a delivery system prior to deployment. Frame material that is not sufficiently stiff may not allow the valve leaflet to function as desired.

Suitable frames may be made from one or more materials and need only be biocompatible or able to be made biocompatible. Examples of suitable materials include, without limitation, stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the frame material includes stainless steel or nitinol.

The frame may have unexpanded and expanded configurations. In one aspect, the expanded configurations can be resiliently further extended in one or more radial directions. In another aspect, a frame can expand from a compressed, or unexpanded, delivery configuration to one or more radially expanded deployment configurations, for example through self expansion or balloon expansion of the frame. The expanded configuration can have any suitable cross-sectional configuration, including circular or elliptical. In one example, the frame can be oriented along the longitudinal axis of a body vessel in the expanded or unexpanded configurations.

In one aspect, the frame is self-expanding. From a compressed configuration, self-expanding frames can expand toward their pre-compression geometry. In some examples, a self-expanding frame can be compressed into a low-profile delivery configuration and then constrained within a delivery system for delivery to a point of treatment in the lumen of a body vessel. At the point of treatment, the self-expanding frame can be released and allowed to subsequently expand to another configuration.

In another aspect, the frame may not be self-expanding. For example, frames may be balloon expandable. In one example, the frame may include a first balloon expandable proximal portion, a second balloon expandable distal portion, and a third frame portion coupling the proximal and distal portions. The third portion may include a valve member coupled thereto.

The dimensions of the implantable frame will depend on its intended use. Typically, the unexpanded dimension of the frame will usually be in the range from about 1 mm to 10 mm, more usually being in the range from 1.5 mm to 6 mm for vascular applications. The expanded dimension will usually be in the range from about 2 mm to 30 mm, preferably being in the range from about 6 mm to 18 mm for vascular applications.

Also provided are examples where the frame comprises a means for orienting the frame within a body lumen. For example, the frame can comprise a marker, such as a radiopaque portion of the frame that would be seen by remote imaging methods such as X-ray, or by detecting a signal from or corresponding to the marker. In other examples, the delivery device can comprise a frame with indicia relating to the orientation of the frame within the body vessel. Additionally, indicia can be located, for example, on a portion of a delivery catheter that can be correlated to the location of the frame within a body vessel.

A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Common radiopaque materials include barium sulfate, bismuth subcarbonate, and zirconium dioxide. Other radiopaque elements include: cadmium, tungsten, gold, tantalum, bismuth, platinum, iridium, and rhodium.

Graft Material

Also provided are aspects wherein the prosthetic valve further comprises a graft material operatively attached to the frame. A wide variety of materials acceptable for use as graft material in implantable medical devices are known in the art, and any suitable material can be utilized. The graft material is preferably a remodelable material and is biocompatible, or able to be made biocompatible.

For example, graft material may include a film, a coating, a sheet of biocompatible fabrics, non-woven materials or porous materials. Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include polymerization of biocompatible polymers from the material surface, coating of the surface with a crosslinked biocompatible polymer, and chemical modification with biocompatible functional groups. Thus, any polymer that may be formed into a porous sheet can be used to make a flexible covering, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above.

Attachment of Prosthetic Valve in Body Vessel

A prosthetic valve according to the present invention may optionally include supplemental attachment means such as anchoring devices, proximal or distal stents, suturing, stapling, searing, bonding, gluing, or otherwise adhering the medical device to the vessel wall or combinations thereof. For example, the prosthetic valve may be secured in place with one or more anchoring devices.

A wide variety of structural features are acceptable for use as anchoring devices, and any suitable structural feature can be used. For example, individual barbs may be used to implant the prosthetic valve into the vessel. The barbs may be secured to the prosthetic valve by any means known to one skilled in the art, including but not limited to welding, stitching, bonding, and adhesives. Desirably, barbs may be attached to the prosthesis frame.

Furthermore, barbs can also comprise separate members attached to the prosthetic valve by suitable attachment means. For instance, barbs can be formed by V-shaped cuts transversing the thickness of a flat metal frame, which are bent outward to form the barb. In some aspects, the number, arrangement, and configuration of the integral barbs can vary according to design preference and the clinical use of the device. The barbs can have any suitable shape, including points or "fish hook"-like configurations. The barbs may or may not penetrate the vessel wall, depending on their design and other factors, including the thickness and type of covering used.

Alternatively or in addition to anchoring devices, bioadhesives may be used for attachment. The bioadhesive can be included in any suitable part of the prosthetic valve. Preferably, the bioadhesive is attached to the abluminal surface of the flexible covering. Selection of the type of bioadhesive, the portions of the prosthetic valve comprising the bioadhesive, and the manner of attaching the bioadhesive to the prosthetic valve can be chosen to perform a desired function upon implantation. For example, the bioadhesive can be selected to promote increased affinity of the desired portion of prosthetic valve to the section of the body vessel against which it is urged.

Bioadhesives for use in conjunction with the present invention include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta (TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivitized with sticky molecules such as arginine, glycine, and aspartic acid, and copolymers.

Furthermore, commercially available bioadhesives that may be used in the present invention include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the prosthetic valve can include one or more bioactive agents. The bioactive agent can be included in any suitable part of the prosthetic valve. Selection of the type of bioactive, the portions of the prosthetic valve comprising the bioactive agent, and the manner of attaching the bioactive agent to the prosthetic valve can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis.

The bioactive materials can be attached to the prosthetic valve in any suitable manner. For example, a bioactive can be combined with a biocompatible polyurethane, impregnated in the valve members, positioned within or on the flexible covering, or attached to the surface of the prosthetic valve.

The bioactive agent can be selected to perform one or more desired biological functions. For example, the frame may comprise a bioactive selected to promote the ingrowth of tissue from the interior wall of a body vessel, such as a growth factor. An anti-angiogenic or antneoplastic bioactive such as paclitaxel, sirolimus, or a rapamycin analog, or a metalloproteinase inhibitor such as batimastaat can be incorporated in or coated on the frame or leaflets mitigate or prevent undesired conditions in the vessel wall, such as restenosis. Many other types of bioactive agents can be incorporated in the prosthetic valve.

Prosthetic valves comprising an antithrombogenic bioactive agent are particularly preferred for implantation in areas of the body that contact blood. For example, an antithromogenic bioactive agent can be coated on the valve member surface. An antithrombogenic bioactive agent is any bioactive agent that inhibits or prevents thrombus formation within a body vessel. The prosthetic valve can comprise any suitable antithrombogenic bioactive agent. Types of antithrombotic bioactive agents include anticoagulants, antiplatelets, and fibrinolytics. Anticoagulants are bioactive materials which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Also particularly preferred are prosthetic valves comprising a thrombolytic bioactive agent. Desirably, the thrombolytic bioactive agent is positioned on the luminal surface of the flexible covering or within the valve members. Thrombolytic agents are used to dissolve blood clots that may adversely affect blood flow in body vessels. A thrombolytic agent is any therapeutic agent that either digests fibrin fibres directly or activates the natural mechanisms for doing so. The medical device can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

Bioactive materials for use in biocompatible coatings further include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

A bioactive agent can be incorporated in or applied to portions of the prosthetic valve by any suitable method that permits adequate retention of the bioactive agent material and the effectiveness thereof for an intended purpose upon implantation in the body vessel. The configuration of the bioactive agent on or in the prosthetic valve will depend in part on the desired rate of elution for the bioactive. Bioactive agents can be coated directly on the prosthetic valve surface or can be adhered to a prosthetic valve surface by means of a coating. For example, an antithrombotic bioactive agent can be blended with a polymer and spray or dip coated on the device surface. For example, a bioactive agent material can be posited on the surface of the prosthetic valve and a porous coating layer can be posited over the bioactive agent material. The bioactive agent material can diffuse through the porous coating layer. The coating layer can also be nonporous wherein the rate of diffusion of the bioactive agent material through the coating layer is controlled by the rate of dissolution of the bioactive agent material in the coating layer.

Delivery of Prosthetic Valves

The prosthetic valves of the present invention can be configured for delivery to a body vessel. For example, a prosthetic valve can be compressed to a delivery configuration within a retaining sheath that is part of a delivery system, such as a catheter-based system. Upon delivery, the prosthetic valve can be expanded, for example, by inflating a balloon from inside the prosthetic valve. The delivery configuration can be maintained prior to deployment of the prosthetic valve by any suitable means, including a sheath, a suture, a tube or other restraining material around all or part of the compressed prosthetic valve, or other methods.

Prosthetic valves can be deployed in a body lumen by means appropriate to their design. The prosthetic valves of the present invention can be adapted for deployment using conventional methods known in the art and employing percutaneous transluminal catheter devices. The prosthetic valves are designed for deployment by any of a variety of in situ expansion means.

In one aspect, the prosthetic valve may be mounted onto a catheter that holds the prosthesis as it is delivered through the body lumen and then releases the prosthetic valve and allows it to self-expand into contact with the body lumen. This deployment is effected after the prosthetic valve has been introduced percutaneously, transported transluminally and positioned at a desired location by means of the catheter. The self-expanding prosthetic valve may be deployed according to well-known deployment techniques for self-expanding medical devices. For example, the prosthesis may be positioned at the distal end of a catheter with a removable sheath or sleeve placed over the prosthetic valve to hold the prosthetic valve in a contracted state with a relatively small diameter. The prosthetic valve may then be implanted at the point of treatment by advancing the catheter over a guidewire to the location of the lesion and then withdrawing the sleeve from over the prosthesis. The prosthetic valve will automatically expand and exert pressure on the wall of the blood vessel at the site of the lesion. The catheter, sleeve, and guidewire may then be removed from the patient.

In one aspect, the prosthetic valve is first positioned to surround a portion of an inflatable balloon catheter. The prosthetic valve, with the balloon catheter inside, is configured at a first, collapsed diameter. The prosthesis and the inflatable balloon are percutaneously introduced into a body lumen, following a previously positioned guidewire. For example, in a rapid exchange procedure, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthetic valve are positioned within the body passageway at the point where the prosthesis is to be placed. Thereafter, the balloon is inflated and the prosthesis is expanded by the balloon portion from the collapsed diameter to a second expanded diameter. After the prosthetic valve has been expanded to the desired final expanded diameter, the balloon is deflated and the catheter is withdrawn, leaving the prosthetic valve in place. The prosthetic valve may be covered by a removable sheath during delivery to protect both the prosthesis and the vessel.

While the terms "contracted" and "compressed" have been used to describe the prosthetic valve as having the small diameter necessary for delivery to an implantation site, it will be appreciated that the terms, especially as applied to pressure-expandable prosthetic valves, should not be used to imply that the tube is under external pressure to provide the tube with a small diameter; i.e., a "contracted" or "compressed" pressure-expandable prosthetic valve may be formed and naturally reside in the "contracted" or "compressed" state until internally pressurized to expand. Therefore, "contracted" and "compressed" are intended only to imply that the prosthetic valve is in a state of having a small diameter relative to an expanded state. It will therefore be appreciated by those skilled in the art that yet other modifications could be made to the provided invention without deviating from its spirit and scope as so claimed.

Methods for delivering a prosthetic valve as described herein to any suitable body vessel are also provided, such as a vein, artery, biliary duct, ureteral vessel, body passage or portion of the alimentary canal.

Methods of Treatment and Prevention

Still other aspects provide methods of treating a subject, which can be animal or human, comprising the step of providing one or more prostheses attached to one or more valve members, as described herein. In some aspects, methods of treatment may also provide the step of delivering a prosthetic valve to a point of treatment in a body vessel, or deploying a prosthetic valve at the point of treatment, wherein the prosthetic valves are as described herein.

Methods for treating and/or preventing certain conditions are also provided, such as venous valve insufficiency, varicose veins, esophageal reflux, restenosis or atherosclerosis. In some aspects, the invention relates to methods of treating venous valve-related conditions.

While many preferred examples discussed herein discuss implantation of a medical device in a vein, other examples provide for implantation within other body vessels. In another matter of terminology there are many types of body canals, blood vessels, ducts, tubes and other body passages, and the term "vessel" is meant to include all such passages.

The invention includes other aspects within the scope of the claims, and variations of all aspects, and is limited only by the claims made by the Applicants.

The invention claimed is:

1. A valve prosthesis for implantation within a body lumen comprising a frame and at least one valve member comprising at least one semi-rigid leaflet and at least one flexible leaflet;
   the at least one semi-rigid leaflet comprising a first portion operatively coupled to the frame and a second portion being free of the frame, the at least one semi-rigid leaflet slanted in a retrograde direction from the second portion to the first portion;
   the at least one flexible leaflet comprising a first portion operatively coupled to the frame and a second portion being free of the frame, the at least one flexible leaflet slanted in a retrograde direction from the first portion to the second portion when at rest;
   the at least one flexible leaflet being moveable between a first position that permits fluid flow in a first direction and a second position in which the at least one flexible leaflet second portion coapts with the at least one semi-rigid leaflet second portion thus substantially preventing fluid flow in a second, retrograde direction.

2. The prosthesis of claim 1, where the flexible leaflet and semi-rigid leaflet comprise a material selected from the group consisting of biocompatible polyurethane, extracellular matrix material, xenogenic biomaterials, autologous tissue, and allogeneic tissue.

3. The prosthesis of claim 1, where the semi-rigid leaflet comprises a material different from the flexible leaflet.

4. The prosthesis of claim 3, where the semi-rigid leaflet further comprises a reinforcing material selected from the group consisting of threads, fibers, meshes, and wires.

5. The prosthesis of claim 4, where the fibers comprise electrospun nanofibers.

6. The prosthesis of claim 1, where the flexible leaflet comprises a surface having a curvature approximate to a curvature of the body vessel wall.

7. The prosthesis of claim 1, where the leaflets have a coaptation region between about 1% to about 25% of the body lumen width.

8. The prosthesis of claim 1, where the at least one semi-rigid leaflet is slanted at an angle between about 0 degrees to about 60 degrees above horizontal and the at least one flexible leaflet is slanted at an angle between about 0 degrees to about 60 degrees below horizontal.

9. The prosthesis of clam 8, where the at least one semi-rigid leaflet is slanted at an angle about equal to the slant angle of the least one flexible leaflet.

10. The prosthesis of claim 1, where the at least one flexible leaflet second portion extends into said body lumen between about 40% to about 75% of the body lumen width.

11. The prosthesis of claim 1, where the at least one semi-rigid leaflet second portion extends into the body lumen between about 25% to about 60% of the body lumen width.

12. The prosthesis of claim 1, where the at least one semi-rigid leaflet and the at least one flexible leaflet have a greater leaflet thickness at the first portion than at the second portion.

13. The prosthesis of claim 1, the semi-rigid leaflet comprising an opening that permits a controlled amount of fluid flow in the second, retrograde direction.

14. The prosthesis of claim 13, where the total area of the opening is less than about 50% of the cross-sectional area of the body lumen at a desired point of treatment in the body lumen.

15. The prosthesis of claim 13, where the total area of the opening is less than about 25% of the cross-sectional area of the body lumen at a desired point of treatment in the body lumen.

16. The prosthesis of claim 13, where the opening is substantially square, substantially triangular, substantially ovoid, or teardrop-shaped.

17. The prosthesis of claim 1, where the frame is radially self-expandable between an unexpanded configuration and an expanded configuration.

18. A valve prosthesis for implantation within a body lumen comprising a radially-expandable frame and at least one valve member comprising a semi-rigid leaflet and a flexible leaflet;
   the semi-rigid leaflet comprising a first portion coupled to the frame and a second portion free of the frame, the semi-rigid leaflet slanted in a retrograde direction from the second portion to the first portion at an angle between about 0 degrees to about 60 degrees above horizontal;
   the flexible leaflet comprising a first portion operatively coupled to the frame and a second portion free of the frame, the flexible leaflet slanted in a retrograde direction from the first portion to the second portion at an angle between about 0 degrees to about 60 degrees below horizontal;
   the flexible leaflet being moveable between a first position that permits fluid flow in a first direction and a second position in which the flexible leaflet second portion coapts with the semi-rigid leaflet second portion thus substantially preventing fluid flow in a second, retrograde direction.

* * * * *